(12) United States Patent
Dai

(10) Patent No.: US 6,712,161 B1
(45) Date of Patent: Mar. 30, 2004

(54) TOOL AND METHOD FOR SOIL SAMPLING

(75) Inventor: Gesheng Dai, Richardson, TX (US)

(73) Assignee: GD Air Testing, Inc., Richardson, TX (US)

( * ) Notice: Subject to any disclaimer, the term of this patent is extended or adjusted under 35 U.S.C. 154(b) by 63 days.

(21) Appl. No.: 10/218,963

(22) Filed: Aug. 14, 2002

Related U.S. Application Data

(60) Provisional application No. 60/342,991, filed on Dec. 21, 2001.

(51) Int. Cl.⁷ .......................... E21B 49/02; A01B 45/02; G01N 1/08; G01N 35/10
(52) U.S. Cl. ...................... 175/58; 175/20; 73/864.31; 73/864.86; 73/864.91; 172/22; 111/92
(58) Field of Search .............................. 175/19, 20, 57, 175/58, 244, 44; 73/864, 864.44, 864.91, 864.81–864.86, 864.31; 172/21, 22, 371; 111/92

(56) References Cited

U.S. PATENT DOCUMENTS

| | | | |
|---|---|---|---|
| 2,288,210 A | 6/1942 | Schlumberger | |
| 2,629,376 A | 2/1953 | Gallice et al. | |
| 2,756,748 A | 7/1956 | Ferguson | |
| 3,151,617 A | 10/1964 | Baum | |
| 3,273,930 A | 9/1966 | Gottfried | |
| 3,464,732 A | 9/1969 | Woodward | |
| 3,497,018 A * | 2/1970 | Shultz et al. | 175/6 |
| 3,515,128 A | 6/1970 | McEvoy | |
| 3,581,956 A | 6/1971 | Reid | |
| 3,865,055 A * | 2/1975 | Gilbaugh | 111/101 |
| 4,234,375 A | 11/1980 | Ciccarello | |
| 4,320,770 A | 3/1982 | Etherington et al. | |
| 4,552,155 A | 11/1985 | Etherington et al. | |
| 4,633,957 A * | 1/1987 | Prost | 172/22 |
| 4,848,484 A * | 7/1989 | Clements | 175/20 |
| 4,884,638 A | 12/1989 | Hoffman | |
| 4,887,413 A * | 12/1989 | Tuckey, Jr. | 53/520 |
| 4,974,682 A * | 12/1990 | Hoffman | 172/22 |
| 5,005,433 A * | 4/1991 | Patton | 73/864.44 |
| 5,108,927 A | 4/1992 | Dorn | |
| 5,343,771 A * | 9/1994 | Turriff et al. | 73/864.44 |
| 5,419,211 A * | 5/1995 | Rodel et al. | 73/864.45 |
| 5,505,098 A * | 4/1996 | Turriff et al. | 73/864.44 |
| 5,517,868 A * | 5/1996 | Turriff et al. | 73/864.44 |
| 5,522,271 A | 6/1996 | Turriff et al. | |
| 5,662,179 A | 9/1997 | Falk | |
| 5,706,904 A | 1/1998 | Turriff et al. | |
| 5,937,953 A * | 8/1999 | Melberg et al. | 175/20 |
| 6,098,724 A * | 8/2000 | Ricker | 175/20 |
| 6,125,948 A * | 10/2000 | David et al. | 175/58 |
| 6,502,491 B2 * | 1/2003 | Borowczak et al. | 83/358 |

* cited by examiner

*Primary Examiner*—David Bagnell
*Assistant Examiner*—Jennifer Gay
(74) *Attorney, Agent, or Firm*—Duane Morris

(57) ABSTRACT

A containment cartridge for extracting and preserving a soil sample comprises a cylindrical sampling barrel for insertion into the soil for collecting a soil sample.

13 Claims, 3 Drawing Sheets

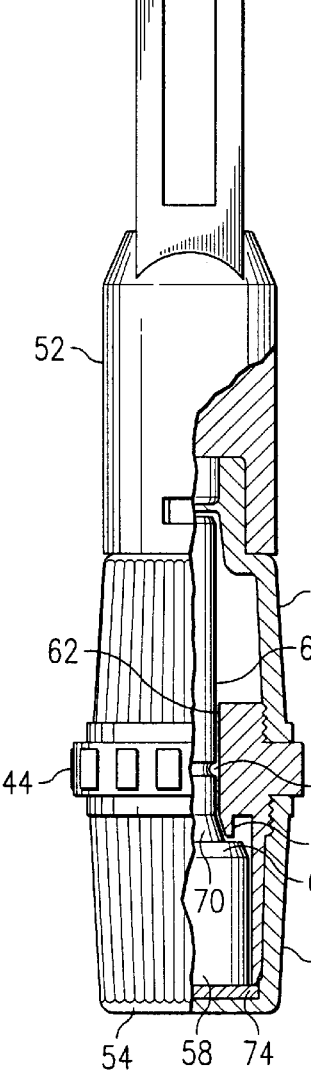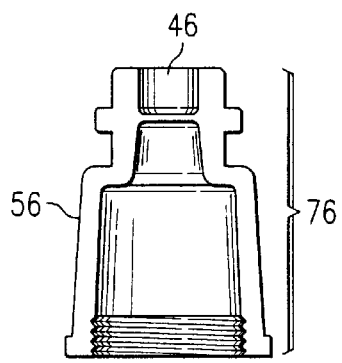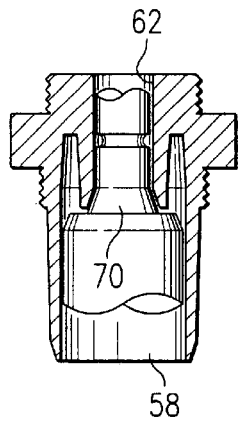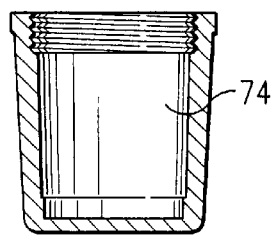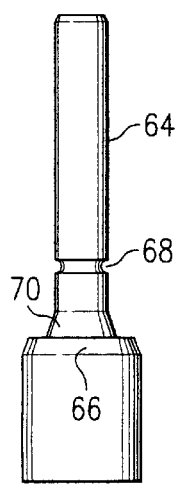
Fig. 6
Fig. 7
Fig. 8
Fig. 9
Fig. 10

TOOL AND METHOD FOR SOIL SAMPLING

CROSS-REFERENCE

This application claims benefits from provisional Patent Application Ser. No. 60/342,991 filed on Dec. 21, 2001, entitled "Tool and Method for Soil Sampling."

BACKGROUND OF THE INVENTION

The present invention relates generally to instruments for measuring and testing, and more particularly, to instruments for sampling soil composition.

Soil sampling tools and devices are used for a variety of purposes, e.g., to obtain samples for soil moisture content or to detect and analyze the composition of the soil. Usually, for various reasons, when a soil sample is required for certain testing, the result of the testing depends in large part upon the availability of high quality test instruments and the ability to preserve the integrity of the obtained soil sample. Preservation of the integrity of the soil sample thus involves (among other factors) preventing evaporation of various volatile elements in the soil sample.

In the conventional art in the industry, various problems exist with respect to soil sampling tools. For example, many sampling tools are made of metal, preferably stainless steel, and tend to be unnecessarily complicated in design. As a consequence, the users have to pay extraordinary cost to acquire such tools.

U.S. Pat. No. 5,505,098 to Turriff et al. (hereinafter "Turriff") proposes a soil sample containment cartridge. However, in practice, this soil sample containment cartridge must be used in connection with two metal handles, one for taking the sample at sites, and another for extracting the sample out in a lab environment. Typically, the metal handle for taking the sample is structurally different from the metal handle for extracting the sample, and they are not functionally interchangeable. It is thus cumbersome to require two different handle tools to complete the sample taking and extracting process.

An improved soil sampling tool which addresses and overcomes disadvantages of prior art tools is greatly desired.

SUMMARY OF THE INVENTION

An improved containment cartridge is disclosed for extracting and preserving a soil sample. The cartridge comprises a cylindrical sampling barrel for insertion into soil for collecting a soil sample wherein the sampling barrel has a holder at the end of the sampling barrel. The holder has a bigger diameter than that of the sampling barrel. The sampling barrel has a rod-like ejector with a disk-like plunger to push the soil sample out from the sampling barrel. The containment cartridge has a first lid securable to a first threaded connection on the sampling barrel at a first side of the holder. The first lid having a concentrically located nipple component with a hole in the center with a predetermined depth. And the nipple component further has a locking slot for further locking a detachable handle tool onto the first lid. The containment cartridge has a second lid securable to a second threaded connection on the sampling barrel at a second side of the holder to seal the soil sample in the sampling barrel after it is collected. The second lid has a sealing septum which isolates the soil sample from the air as the second lid is secured to the sampling barrel. The containment cartridge is used in the field for collection and sealing a soil sample therein and transporting the same to a lab environment. In the lab environment, after the second lid is detached from the sampling barrel, the first lid is detached and reversed to put the ejector in the hole of the first lid so that a force can be applied onto a rim of the first lid to push the ejector downwards, thereby retrieving the collected soil sample from the sampling barrel without securing any handle to the cartridge.

The present invention as described above thus provides an improved soil sampling instrument. The present invention has new features facilitating sample preservation, storage, transportation and identification. For instance, after the soil sample is extracted, there is no need to affix a handle on the entire cartridge to retrieve the soil sample. Since the amount of soil sample in the sampling barrel is relatively small, the top lid serves as a handle for a user to extract the soil sample out, and therefore significantly eases the lab use of the sampling instrument. Moreover, the entire sampling instrument can be made out plastic so that the cost of the instrument can be significantly less expensive than the conventional stainless steel set.

BRIEF DESCRIPTION OF THE DRAWINGS

FIG. 6 is a front view of a soil sampling instrument including an interior view of half of the instrument according to another example of the present invention.

FIG. 7 is a sectional view of the top lid of the instrument.

FIG. 8 is a sectional view of the sampling barrel and the guiding passage of the instrument.

FIG. 9 is a sectional view of the bottom lid of the instrument.

FIG. 10 shows a front view of an ejector of the instrument.

DESCRIPTION OF THE PREFERRED EMBODIMENT

The present invention provides a soil sampling instrument that only requires one type of handle to work with an improved soil sample containment cartridge to extract soil samples in the field, and does not require a handle of any kind to retrieve the collected soil samples in the lab environment.

Figure 1:
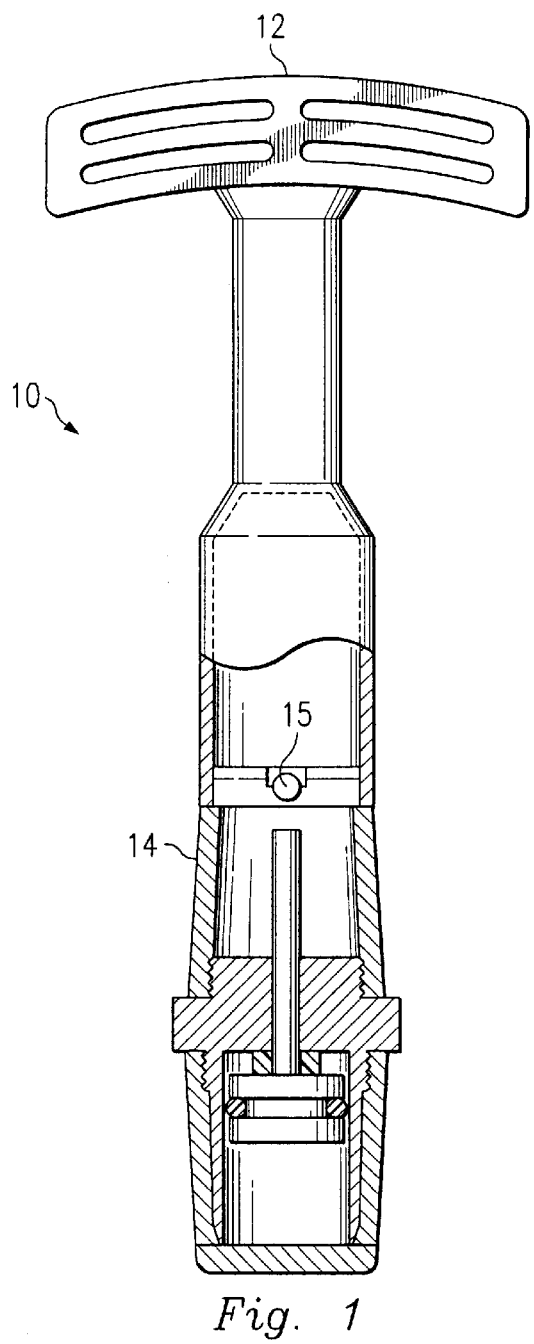
FIG. 1 illustrates a soil sampling instrument including two detachable components: an extended handle module and a containment cartridge according to one example of the present invention.
Figure 2:
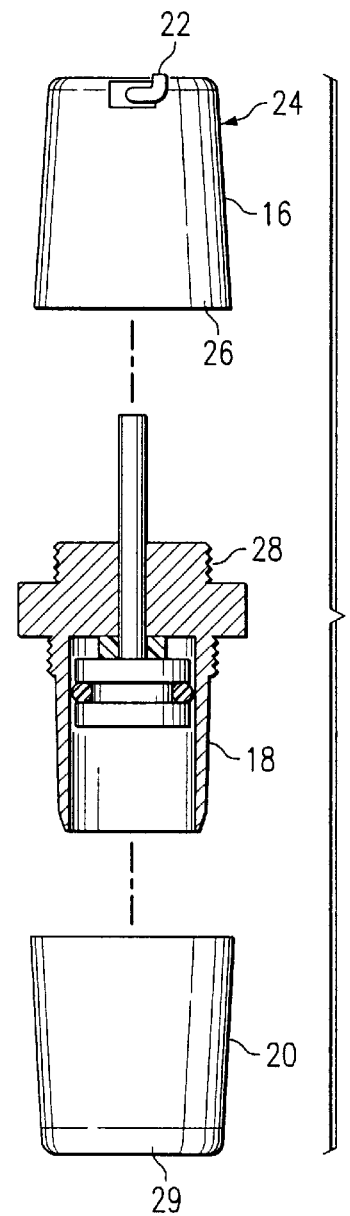
FIG. 2 illustrates three detachable components of the containment cartridge of FIG. 1.
Figure 3:
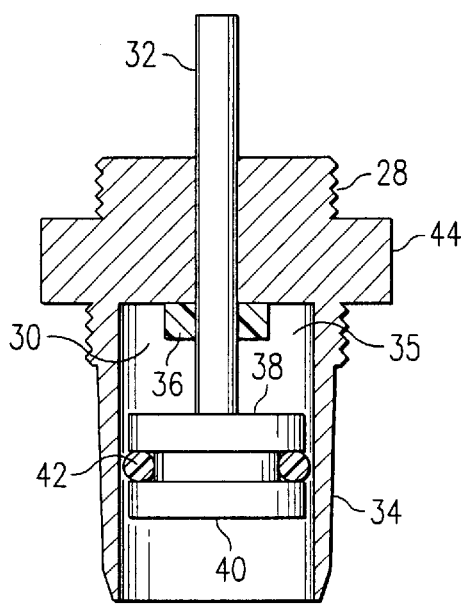
FIG. 3 is a representative sectional view showing the interior of a sampling barrel of the containment cartridge of FIG. 2.

FIG. 1 illustrates a soil sampling instrument 10 including two detachable components: an extended handle module 12 and a containment cartridge 14. Referring further to FIG. 2 wherein the containment cartridge 14 is further illustrated with three detachable components: a top lid 16, sampling barrel 18, and bottom lid 20. FIG. 3 is a detailed sectional view of the sampling barrel 18.

Referring back to FIG. 2, the top lid 16 has two locking slots 22 situated on the surface of one nipple end 24, a first part of the locking slot 22 is parallel to the axis of the top lid, and the second part of which is at an angle to the first part.

When a protruding element 15 (FIG. 1) such as a small cylindrical notch is inserted into the first part of the locking slot 22, and turned to fit in the second part of the locking slot, the elongate, tube-like, T-shaped handle module 12 is now concentrically secured to the containment cartridge 14. It is understood that many other similar connection mechanisms can be implemented to secure the top lid 16 with the extended handle module 12. For instance, simply designing a threaded area on the upper part of the top lid and matching the threaded area at the bottom of the extended handle will connect the two components together. It is also noted that the nipple end 24 has two functions. One, it is smaller than the diameter of the top lid so that it is easier to insert a rod-like ejector (which will be explained below in FIG. 3) into a contained hole area in the nipple end. Two, it increases the strength of the top lid to server as a "pusher" of the ejector (which is also explained below). Since taking soil samples only requires a vertical force to push the containment cartridge into the soil, applying a force on the extended handle module 12 would not accidentally separate the handle module 12 from the containment cartridge 14. Even if it requires some minor rotational movements, the connection between the extended handle and the containment cartridge will not be deconstructed. In fact, in this immediate example, a user can even twist the handle clockwise toward the second part of the locking slot while applying the force downward to push the containment cartridge into the soil.

At a distal end of the top lid 16, there are grooves 26 (or threaded interior area) to secure the top lid 16 with matching threads 28 on a connecting end of the sampling barrel 18. The bottom lid 20 contains a rubber or plastic septum 29 which is designed to seal off the soil sample in the sampling barrel 18 when the sampling barrel is "screwed into" the bottom lid 20. Because this septum is in a direct contact with the "mouth piece" of the sampling barrel 18, it does not leave any space for the soil sample to evaporate, thereby achieving the best sealing effect.

Referring to FIG. 3, the interior region 30 of the sampling barrel 18 contains a rod-like ejector 32 connecting to a disc-like plunger 34. The plunger 34 and the ejector 32 are all preferably cylindrical and are actually preferred to be molded as one piece instead of two separate pieces. The sampling barrel has a passage 35 extending along its length for receiving the rod-like ejector 32. The passage 35 and ejector 32 are all preferably circular in cross-sectional shape. The diameters of the passage 35 and the ejector 32 are cooperatively selected to provide slight clearance therebetween so that the ejector 32 may move freely within the passage 35.

The interior height of the top lid 16 needs to be high enough to accommodate the movement of the ejector 32 because when the cartridge is pushed against a soil level, the soil pushes the plunger 34 back up. In one example, inside the interior portion of the sampling barrel 18, and centrally situated around the ejector 32 is a stopper 36, which is formed from the interior wall of the sampling barrel 18. By designing the protruding length of the stopper 36 appropriately so that the ejector 32 stops at a predetermined location, the cartridge 14 takes in a known amount of soil for sampling every time it is used. The plunger 34 is actually formed by three layers of material. The top and bottom layers (38 and 40) are made of plastic which is the same piece as the ejector 32. A rubber ring 42 is positioned between the top and bottom layers (38 and 40), which have a slightly larger diameter than those of the top and bottom layers. The diameter of the rubber ring 42 is selected so that it is in close contact with the interior wall of the sampling barrel to prevent any leakage of soil to the upper portion of the sampling barrel beyond the rubber ring 42. Between the interior region 30 and the connecting end of the sampling barrel 18, there is a ring of grooved holder 44. The holder 44 is designed to allow the user to hold it and twist open or close either the top lid 16 or the bottom lid 20. As stated above, the bottom lid 20 is for sealing the soil sample inside the sampling barrel 18 after the soil sample is extracted. The advantage of using the bottom lid is that a sealing and labeling tape can further circle around between the bottom lid 20 and the grooved holder 44.

Figure 4:
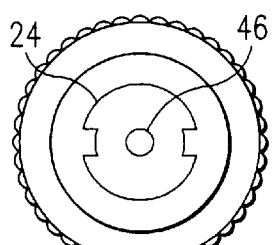
FIG. 4 is a top view of the containment cartridge of FIG. 1.
Figure 5:
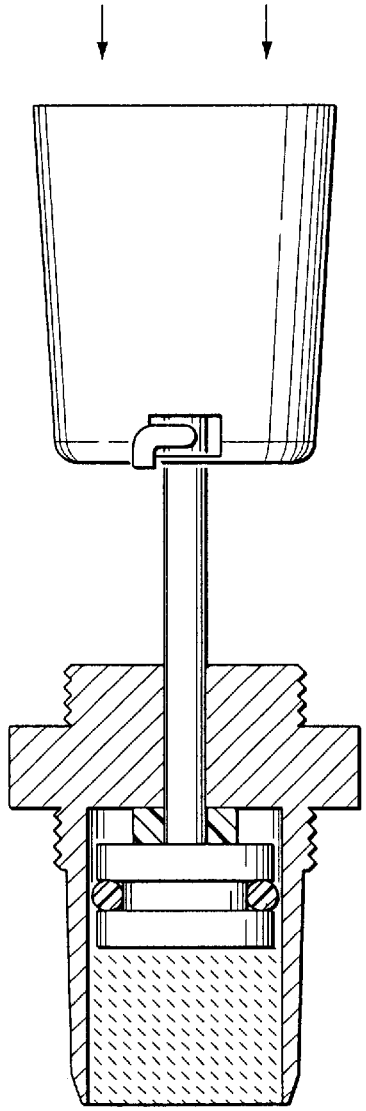
FIG. 5 is a front view of using a top lid of the containment cartridge to assist retrieving the soil sample in the containment cartridge.

FIG. 4 is a top view of top lid 16 of the containment cartridge 14. A receptive hole 46 with a predetermined depth and diameter is made in the nipple end. The receptive hole 46 is used to receive the rod-like ejector 32, and push out the soil sample contained in the sampling barrel in a lab environment. FIG. 5 illustrates how the top lid 16 is reversed, and put on the ejector so that a user in the lab can push the rim of the top lid 16 to extract the soil sample. This is a significant improvement over the prior art since there is no need to use another handle at all. The containment cartridge 14 delivered to the lab will be self-sufficient for extracting the soil out from the sampling barrel. This containment cartridge does not need additional handles to be used in the lab environment, thus reducing the cost to maintaining the extracting tools in the lab as well as simplifies the soil sample extracting process.

By using soil sampling instrument disclosed according to the present invention, a new method for collecting a soil sample 24 is also introduced. When a field user needs to take a soil sample, he only needs to take one extended handle module with him since it can be used with multiple containment cartridges 14. The containment cartridge 14 has both the top lid 16 and bottom lid 20 secured thereon before the user handles it to ensure that the containment cartridge is not contaminated. The user can simply insert and twist the handle module clockwise into the locking slot 22 on the nipple portion 24 of the containment cartridge 14 to secure the handle module to the cartridge. Then, the user holds on to the handle module and the top lid of the containment cartridge, and unscrew the bottom lid 20 off from the containment cartridge. The mouth piece or open end of the sampling barrel is now ready to be pushed into a soil ground for extracting a soil sample. The soil sample pushes the plunger 34 back until it is stopped by the stopper 36, and the entire sampling barrel is taken out from the soil, and immediately sealed with the bottom lid being screwed thereon. The user then holds the entire containment cartridge 14 in one hand, and uses the other hand to twist the handle module 12 counterclockwise and pulls it off the cartridge. Now the containment cartridge 14 is back to its initial state except that it now has the soil sample contained therein. A piece of sealing and labeling tape can be put on to further seal off the containment cartridge 14. This labeled containment cartridge 14 is then shipped to a predetermined lab for retrieving the soil sample. In the lab, a lab user needs no additional tools such as the handle module to retrieve the soil sample. She holds on the holder 44 and unscrews the top lid 16 off first, and does the same to the bottom lid 20 to expose the contained soil sample. She reverses the top lid 16, puts the rod-like ejector into the receptive hole 46, and pushes the ejector downward so that the soil are now unloaded from the sampling barrel 18.

FIG. 6 is a front view of a soil sampling instrument 50 including an interior view of half of the instrument according to another example of the present invention. As the soil sampling instrument 10, the soil sampling instrument 50 includes two detachable components: the extended handle module 52 and a containment cartridge 54 which further containing a top lid 56, sampling barrel 58, and bottom lid 60. Although the top lid 56 is marked differently from the top lid 16 (FIG. 1), it is understood that they can be the same design and functionally the same. Similar to the cartridge illustrated in FIG. 1, the containment cartridge 54 has a holder 44 to allow both the top lid 56 and the bottom lid 60 to be secured thereon. The holder 44 may be grooved and is around the periphery of the cartridge. As described along with FIG. 1, the holder allows both the top and bottom lids to be secured thereon, and is typically around the upper end of the sampling barrel. In the upper portion of the containment cartridge 54, there is a guiding passage 62 extending along the length for receiving an ejector 64 which is in connection with a disc-like plunger 66. The guiding passage 62, in one example, is cylindrical in shape to host the ejector for a predetermined distance. As such, the ejector 64 is preferably cylindrical generally, and is actually preferred to be molded as one piece with the plunger. The diameters of the guiding passage 62 and the ejector 64 are close to each other, and are cooperatively selected to provide slight clearance therebetween so that the ejector 64 may move freely within the guiding passage 62. At a predetermine place on the ejector 64, a groove 68 is carved out to receive a rubber ring. The ejector 64 equipped with the rubber ring seals off any significant gap between the ejector 64 and the interior wall of the guiding passage 62 while still allowing the ejector moves in and out along the guiding passage. Since the sampling instrument 50 is going to receive soil inside the sampling barrel 58, and there may be a gap between the plunger 66 and the interior wall of the sampling barrel 58, by implementing such a sealing mechanism within the guiding passage actually reduces any possibility of leaking volatile elements of the soil. In addition to the sealing mechanism in the guiding passage area, there is an internal taper 70 connecting between the ejector 64 and the plunger 66 which in conjunction with a taped sealing node 72 further prevents any volatile elements to escape through the upper half of the containment cartridge 54. The design of the sealing node 72 and the taper 70 is such that the harder the plunger is pushed upward, the tighter the conical surface of the taper gets against the sealing node due to the gradual change in diameter of the internal taper, thereby creating another sealing mechanism. In addition, the taped sealing node 72 also serves as a stopper to hold the plunger 66 at the top of the sampling barrel 58.

Inside of the lid 60, there is a polytetrafluroethylene liner 74, i.e. TEFLON, further seals the soil sample in the sampling barrel 58 after the lid is screwed on the sampling barrel. Due to the non-reactive nature of the Teflon liner 74, any chemical elements contained in the soil sample will not be contaminated. In another example, the interior wall of the sampling barrel can be coated with prevention materials to reduce the possibility of having any chemical reaction or contamination between the soil and the material of the sampling barrel. Because the sealing mechanisms at the guiding passage part and the tapped joint part, there is no requirement to reduce the space between the plunger and the interior wall of the sampling barrel to seal the soil sample therein. As such, there is no friction created between the plunger and the interior wall of the sampling barrel, and the integrity of the coated interior wall can be maintained. On the other hand, if the sealing mechanism is implemented around the plunger, the protection coating may become ineffective.

FIG. 7 is a sectional view of the top lid 56. The top lid 56 has an internal height 76 high enough to host a protruding ejector while the plunger is pushed all the way up. The top lid 56 also has the receptive hole 46 for receiving the ejector for pushing thereof.

FIG. 8 is a sectional view of the sampling barrel 58 and the guiding passage 62. Also shown in this FIG. 8 is the tapped sealing node 70.

FIG. 9 is a sectional view of the bottom lid 60 wherein the Teflon liner is placed at the tip of the lid.

FIG. 10 shows a front view of the ejector 64 with the groove 68 for receiving a rubber ring, the plunger 66, and the tapped joint 70.

The soil sampling instrument as described above with regard to FIG. 6 can improve the soil sampling process in the field. For example, when the soil sampling instrument is shipped to the user, the plunger 66 has been pushed all the way to the upper portion of the sampling barrel with the top lid covering thereof. In addition, since the rubber ring on the ejector 64 is in close contact with the guiding passage, both sealing mechanisms are securely applied. As such, there is no requirement for the user to push the soil sample tightly against the plunger in order to use the upper surface (or back surface) of the plunger to seal off the gap between the plunger and the guiding passage. However, in order to minimize any possible contamination, the bottom lid 60 is already put on. When the user is ready to take the soil sample, she takes off the lid, the top lid is inserted into a handle module using a locking mechanism (e.g., an insert-and-turn locking mechanism), and the user holding the handle module can push the empty sampling barrel to the ground. Since the intake of the soil sample does not need to push the plunger up, it is a far easier process to get the soil sample comparing to conventional tools which require the soil sample to propel the plunger up. Once the soil sample is in the sampling barrel, the bottom lid 60 is put back on with the Teflon liner covering the open end of the sampling barrel. When the cartridge is shipped to a lab environment, the bottom lid 60 is opened and reversed, and, as described above, pushes the rod-like ejector to extract the soil sample from the sample barrel.

The present invention, as described above, thus provides an improved soil sampling instrument. The present invention has new features facilitating sample preservation, storage, transportation and identification. For instance, after the soil sample is extracted, there is no need to affix a handle to retrieve the soil. The top lid serves the function of an extended handle, and thus significantly eases the lab use of the sampling instrument. The septum contained inside the bottom lid isolates the obtained soil sample from the air, thereby maintaining the integrity of the obtained sample during further transportation of the containment cartridge. Moreover, the entire sampling instrument can be made out plastic so that the cost of the instrument can be significantly less expensive than the conventional stainless steel set.

The above disclosure provides many different embodiments, or examples, for implementing different features of the invention. Specific examples of components, and processes are described to help clarify the invention. These are, of course, merely examples and are not intended to limit the invention from that described in the claims.

While the invention has been particularly shown and described with reference to the preferred embodiment thereof, it will be understood by those skilled in the art that various changes in form and detail may be made therein without departing from the spirit and scope of the invention, as set forth in the following claims.

What is claimed is:

1. A cartridge for extracting and preserving a soil sample, the cartridge comprising:
   a cylindrical sampling barrel for insertion into soil for collecting a soil sample, the sampling barrel having a holder at the end of the sampling barrel, the holder having a bigger diameter than that of the sampling barrel, the sampling barrel having a rod-like ejector with a disk-like plunger to push the soil sample out from the sampling barrel;
   a first lid securable to a first threaded connection on the sampling barrel at a first side of the holder, the first lid having a concentrically located nipple component with a receptive hole in the middle of the top of the nipple component with a predetermined depth, the nipple component further having a locking slot for locking a detachable handle tool onto the first lid; and
   a second lid securable to a second threaded connection on the sampling barrel at a second side of the holder to seal the soil sample in the sampling barrel after it is collected by a septum positioned inside the second lid,
   wherein after the second lid is detached from the sampling barrel, the first lid is detached and reversed to put the ejector in the receptive hole of the first lid so that a force can be applied on to a rim of the first lid to push the ejector downwards, thereby retrieving the collected soil sample from the sampling barrel without the assistance of securing any handle to the cartridge.

2. The cartridge of claim 1 wherein the height of the first lid is determined based on how far the ejector is to be pushed back into the first lid while collecting the soil sample.

3. The cartridge of claim 2 wherein the sampling barrel has a stopper concentrically located with the ejector inside the sampling barrel stopping the ejector to be pushed beyond a predetermined point.

4. A method for obtaining a soil sample using a cylindrical sampling barrel, the method comprising:
   securing a first lid to a first threaded connection on the sampling barrel at a first side of a holder of the sampling barrel, the holder having a bigger diameter than that of the sampling barrel, the first lid having a concentrically located nipple component with a receptive hole in the middle of the top of the nipple component with a predetermined depth;
   connecting an extended handle to the nipple component through a locking mechanism for locking the extended handle onto the first lid;
   inserting, using the extended handle, the sampling barrel into the soil for collecting the soil sample, wherein the soil sample pushes a rod-like ejector with a disk-like plunger inside the sampling barrel toward the first lid;
   pulling the sampling barrel out from the soil;
   securing a second lid to a second threaded connection on the sampling barrel at a second side of the holder to seal the soil sample in the sampling barrel after the sampling barrel is pulled using a septum positioned inside the second lid;
   unlocking the extended handle from the first lid;
   transporting the soil sample inside the sample barrel sealed with the first and second lids to a predetermined location for retrieving same;
   removing the second lid from the sampling barrel;
   removing the first lid from the sampling barrel;
   reversing the removed first lid to position the receptive hole to hold the ejector; and
   pushing the soil sample out from the sampling barrel by exerting force on a rim of the reversed first lid to press the ejector,
   wherein the pressed ejector pushes the soil sample out from the sampling barrel without the assistance of securing any handle to the sampling barrel.

5. The method of claim 4 further comprising sealing the sampling barrel with the second lid with sealing tapes before the sampling barrel is transported.

6. The method of claim 4 further comprising labeling the sampling barrel before the sampling barrel is transported.

7. A cartridge for extracting and preserving a soil sample, the cartridge comprising:
   a cylindrical sampling barrel for insertion into soil for collecting a soil sample;
   a guiding passage connected at a first end of the sampling barrel and being coaxial with the sampling barrel for hosting a rod-like ejector, the ejector being connected to a disk-like plunger through an internal taper having a conical surface, the diameter of the guiding passage being substantially smaller than that of the sampling barrel, and the rod-like ejector having an o-ring therearound to minimize the space between the ejector and the guiding passage;
   a holder on the periphery of the cartridge and around the first end of the sampling barrel;
   a first lid securable to a first threaded connection on the cartridge at a first side of the holder, the first lid having a concentrically located nipple component with a receptive hole in the middle of the top of the nipple component with a predetermined depth, the nipple component further having a locking slot for locking a detachable handle tool onto the first lid; and
   a second lid securable to a second threaded connection on the cartridge at a second side of the holder to seal the soil sample in the sampling barrel by having a Teflon septum positioned inside the second lid,
   wherein the internal taper seals the air gap between the sampling barrel and the guiding passage, the sealing of which is further reinforced by the o-ring around the ejector,
   wherein after the second lid is detached from the sampling barrel, the first lid is detached and reversed to put the ejector in the receptive hole of the first lid so that a force can be applied on a rim of the first lid to push the ejector downwards, thereby retrieving the collected soil sample from the sampling barrel without the assistance of securing any handle to the cartridge.

8. A cartridge for extracting and preserving a soil sample, the cartridge comprising:
   a cylindrical sampling barrel for insertion into soil for collecting a soil sample;
   a guiding passage at a first end of the sampling barrel and being coaxial with the sampling barrel for hosting a rod-like ejector connected to a disk-like plunger through an internal taper, the diameter of the guiding passage being substantially smaller than that of the sampling barrel, and the rod-like ejector having an o-ring therearound to minimize the space between the ejector and the guiding passage; and
   a first lid securable to a first threaded connection on the cartridge, the first lid having a concentrically located nipple component with a receptive hole in the middle of the top of the nipple component with a predetermined depth, the diameter of the receptive hole being bigger than the diameter of the ejector, wherein the internal taper seals the air gap between the sampling barrel and the guiding passage while the plunger is pushed tightly toward the guiding passage, the sealing of which is further reinforced by the o-ring around the ejector, wherein, when the collected soil sample is ready to be extracted from the cartridge, the first lid is detached and reversed to put the ejector in the receptive hole so that a force can be applied on a rim of the first lid to push the ejector downwards, thereby retrieving the collected soil sample from the sampling barrel without the assistance of securing any handle to the cartridge.

9. The cartridge of claim 8 further comprising a holder on the periphery of the cartridge and close to the first threaded connection for providing a firm grip of a user when the user secures the first lid to or detaches the lid from the cartridge.

10. The cartridge of claim 8 further comprising a second lid securable to a second threaded connection for sealing the soil sample in the sampling barrel.

11. The cartridge of claim 10 wherein the second lid has a polytetrafluroethylene septum positioned inside the second lid.

12. The cartridge of claim 8 wherein the nipple component further includes a locking slot for locking a detachable handle tool onto the first lid.

13. A method for extracting a soil sample using a containment cartridge, the cartridge a cylindrical sampling barrel, a guiding passage connected at a first end of the sampling barrel and being coaxial with the sampling barrel for hosting a rod-like ejector, the ejector being connected to a disk-like plunger through an internal taper having a conical surface, and the rod-like ejector having an o-ring therearound to minimize the space between the ejector and the guiding passage, the method comprising:

providing a user the cartridge with the plunger pushed tightly toward the guiding passage;

securing a sampling handle tool to a first lid secured to a first threaded connection on the cartridge, the first lid having a concentrically located nipple component with a receptive hole in the middle of the top of the nipple component with a predetermined depth, the nipple component further having a locking slot for locking the handle tool onto the first lid;

detaching a second lid initially secured to a second threaded connection on the cartridge to expose an opening of the sample barrel;

inserting the sampling barrel into a soil sampling area by applying a force on the sampling handle tool;

retrieving the sampling barrel back from the soil sampling area;

sealing the soil sample in the sampling barrel by securing the second lid back onto the cartridge, the second lid having a polytetrafluroethylene septum positioned inside the second lid;

detaching the sampling handle tool from the cartridge;

transferring the cartridge to a predetermined area for extracting the soil sample;

detaching the second lid from the cartridge;

detaching the first lid and reversing it to put the ejector in the receptive hole of the first lid; and applying a force on a rim of the first lid to push the ejector, thereby retrieving the collected soil sample from the sampling barrel without the assistance of securing any handle to the cartridge.

* * * * *